United States Patent
Nick et al.

(10) Patent No.: US 11,622,708 B2
(45) Date of Patent: Apr. 11, 2023

(54) LOW-NOISE MULTI-CHANNEL VOLTAGE RECORDING DEVICE

(71) Applicant: META PLATFORMS TECHNOLOGIES, LLC, Menlo Park, CA (US)

(72) Inventors: Teresa Ann Nick, Woodland Hills, CA (US); Ravi Patel, Redondo Beach, CA (US); Michael Maridakis, Garden Grove, CA (US); Stefanie Hutka, Los Angeles, CA (US); Laura Berman, Venice, CA (US); Arye Barnehama, Venice, CA (US)

(73) Assignee: Meta Platforms Technologies, LLC, Menlo Park, CA (US)

( * ) Notice: Subject to any disclaimer, the term of this patent is extended or adjusted under 35 U.S.C. 154(b) by 1610 days.

(21) Appl. No.: 15/059,129

(22) Filed: Mar. 2, 2016

(65) Prior Publication Data

US 2017/0251945 A1    Sep. 7, 2017

(51) Int. Cl.
*A61B 5/291*    (2021.01)
*A61B 5/00*    (2006.01)
(Continued)

(52) U.S. Cl.
CPC .......... *A61B 5/291* (2021.01); *A61B 5/0022* (2013.01); *A61B 5/0077* (2013.01); *A61B 5/165* (2013.01); *A61B 5/6898* (2013.01); *A61B 5/721* (2013.01); *A61B 5/743* (2013.01); *G06V 10/147* (2022.01); *G06V 20/20* (2022.01); *G16H 40/67* (2018.01);
(Continued)

(58) Field of Classification Search
CPC ... A61B 5/7278; A61B 5/0478; A61B 5/0402; A61B 5/0408; A61B 5/04085; A61B 5/0488; A61B 5/721; A61B 5/743; A61B 5/291; A61B 5/0022; A61B 5/0077; A61B 5/165; A61B 5/6898; A61B 5/398; A61B 5/318; A61B 5/389; A61B 5/01; A61B 5/1038; A61B 5/1118; A61B 2560/0242; A61B 2562/0204; A61B 2562/0219;
(Continued)

(56) References Cited

U.S. PATENT DOCUMENTS

2002/0026112 A1* 2/2002 Nissila ................. A61B 5/0408
600/372
2011/0282179 A1* 11/2011 Zdeblick ................. A61N 1/05
600/393

(Continued)

OTHER PUBLICATIONS

Acharya, Venkatesh, "Improving Common-Mode Rejection Using the Right-Leg Drive Amplifier", Texas Instruments—Application Report SBAA188, (Jul. 2011), 11 pgs.
(Continued)

*Primary Examiner* — Eun Hwa Kim
*Assistant Examiner* — Catherine Premraj
(74) *Attorney, Agent, or Firm* — Fenwick & West LLP

(57) ABSTRACT

A system and method for a multichannel voltage recording device is described. A multichannel voltage recording device comprises at least three electrodes disposed across a conductive material. The electrodes are configured to be coupled to a skin of a user. A frame comprises the conductive material that is configured to receive a driven right leg (DRL) signal based on the voltage signals from the at least three electrodes.

10 Claims, 11 Drawing Sheets

(51) Int. Cl.
| | |
|---|---|
| *A61B 5/16* | (2006.01) |
| *G16H 40/67* | (2018.01) |
| *G16Z 99/00* | (2019.01) |
| *G06V 10/147* | (2022.01) |
| *G06V 20/20* | (2022.01) |
| *A61B 5/103* | (2006.01) |
| *A61B 5/11* | (2006.01) |
| *A61B 5/01* | (2006.01) |
| *A61B 5/318* | (2021.01) |
| *A61B 5/389* | (2021.01) |
| *A61B 5/398* | (2021.01) |

(52) U.S. Cl.
CPC ............... *G16Z 99/00* (2019.02); *A61B 5/01* (2013.01); *A61B 5/1038* (2013.01); *A61B 5/1118* (2013.01); *A61B 5/318* (2021.01); *A61B 5/389* (2021.01); *A61B 5/398* (2021.01); *A61B 2560/0242* (2013.01); *A61B 2562/0204* (2013.01); *A61B 2562/029* (2013.01); *A61B 2562/0219* (2013.01); *A61B 2562/043* (2013.01)

(58) Field of Classification Search
CPC ........ A61B 2562/029; A61B 2562/043; G16H 40/67; G06F 19/00; G06K 9/00671; G06K 9/209
See application file for complete search history.

(56) References Cited

U.S. PATENT DOCUMENTS

| | | | | |
|---|---|---|---|---|
| 2013/0172719 | A1* | 7/2013 | Sakai | A61B 5/02438 600/382 |
| 2013/0261423 | A1* | 10/2013 | Herrala | A61B 5/0488 600/393 |
| 2014/0100432 | A1* | 4/2014 | Golda | A61B 5/04325 600/301 |
| 2014/0336473 | A1* | 11/2014 | Greco | A61B 5/02055 600/301 |
| 2015/0165269 | A1* | 6/2015 | Herrala | A63B 24/0062 482/8 |
| 2015/0305686 | A1* | 10/2015 | Coleman | A61B 5/7264 600/301 |

OTHER PUBLICATIONS

Winter, Bruce B., "Driven-Right-Leg Circuit Design", IEEE Transactions on Biomedical Engineering, vol. BME-30, No. 1 (Jan. 1983), 5 pgs.

* cited by examiner

LOW-NOISE MULTI-CHANNEL VOLTAGE RECORDING DEVICE

BACKGROUND

The subject matter disclosed herein generally relates to acquisition of biometric data. Specifically, the present disclosure addresses systems and methods for measuring and recording multichannel voltage data.

One problem with biometric feedback of oscillatory phenomena, such as electroencephalography (EEG) and electrocardiography (ECG), is common-mode interference. Biometric feedback uses biological signal amplifiers that measure very small amplitude electrical signals emitted by the human body. Unfortunately, the human body can act as an antenna and pick up electromagnetic interference (EMI). This interference can obscure the biological signals, making them very hard to measure. One solution is to apply a Driven Right Leg (DRL) circuitry to eliminate interference noise by actively canceling the interference. However, DRL signal may not be evenly distributed with multiple electrodes positioned in close adjacent areas. In those circumstances, the circuit tends to oscillate, likely due to imbalances in the DRL compensation and feedback cycling.

BRIEF DESCRIPTION OF THE SEVERAL VIEWS OF THE DRAWINGS

To easily identify the discussion of any particular element or act, the most significant digit or digits in a reference number refer to the figure number in which that element is first introduced.

DETAILED DESCRIPTION

Description

Figure 1:
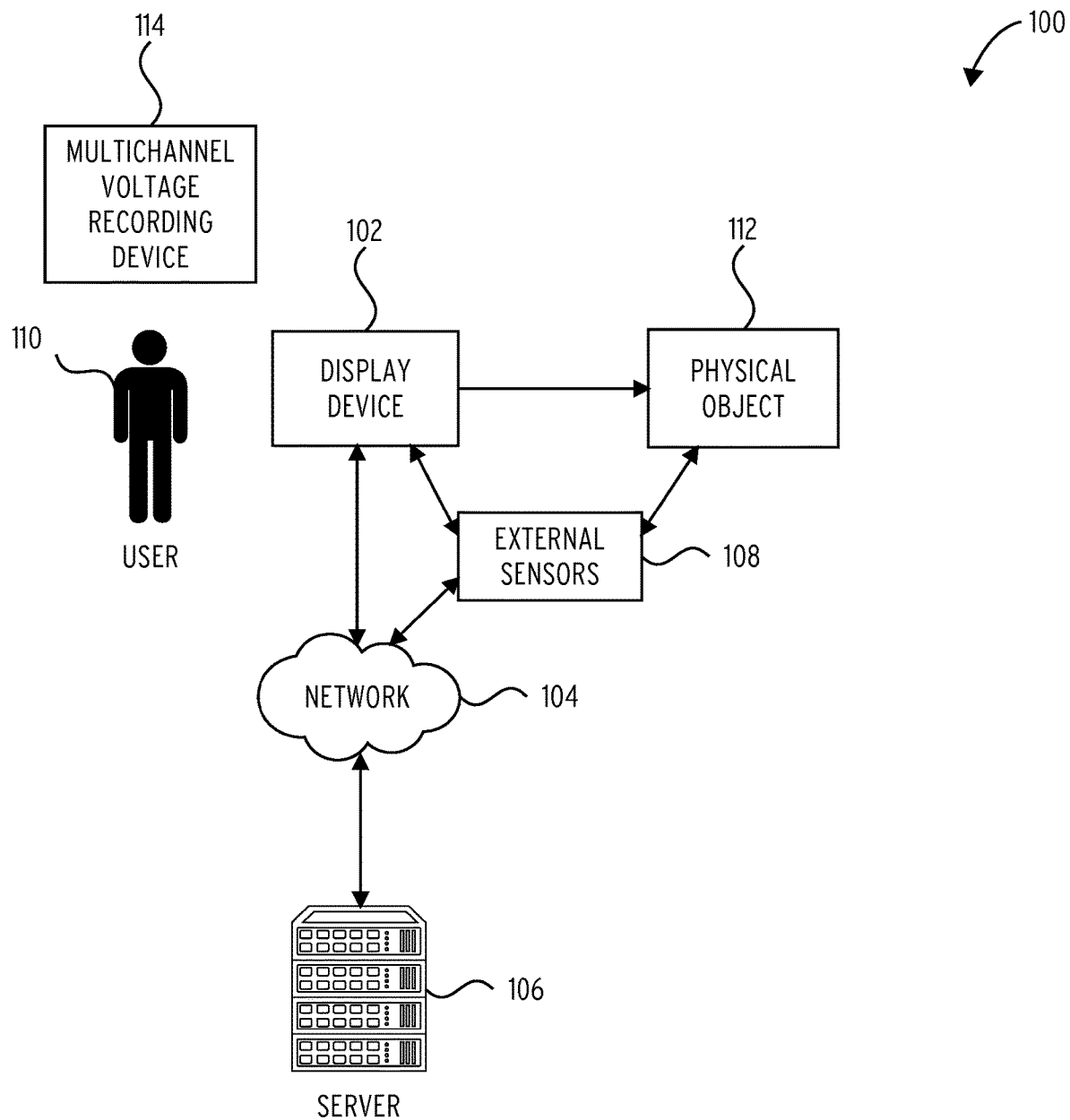
FIG. 1 is a block diagram illustrating an example of a network environment suitable for a multi-channel voltage recording device, according to some example embodiments.

Example methods and systems are directed to a multichannel voltage recording device. Examples merely typify possible variations. Unless explicitly stated otherwise, components and functions are optional and may be combined or subdivided, and operations may vary in sequence or be combined or subdivided. In the following description, for purposes of explanation, numerous specific details are set forth to provide a thorough understanding of example embodiments. It will be evident to one skilled in the art, however, that the present subject matter may be practiced without these specific details.

A Driven Right Leg (DRL) circuit active can be used as a noise compensation circuit in voltage recording devices such as EEG. However, the close placement or close proximity of recording electrodes can result in oscillatory activity characteristic, especially for electrodes or circuits with small form factor designs.

The present application describes a multichannel voltage recording device with high quality recording from adjacent areas using a palm-sized device, for example, to monitor and detect activity differences and similarities in two brain hemispheres. Hemispheric asymmetry is known to correlate with certain behavioral states, such as stress, and with certain pathological conditions, such as schizophrenia and depression. Thus, the present multichannel voltage recording device can be used to accurately detect stress or, potentially, diagnose mental illness. Other possible applications include the detection of certain heart abnormalities and zones of skeletal muscle weakness.

Furthermore, the present recording device can be deployed using a DRL circuit (B. B. Winter and J. G. Webster, "Driven-right-leg circuit design," IEEE Trans. Biomed. Eng., no. 1, pp. 62-66, 1983) using the Texas Instruments ADS1294 chip (other circuits may also be used to implement this same technology). Voltage recordings are made through at least three electrodes. For example three electrodes (RightSignal, CentralReference, and LeftSignal) are evenly spaced (across a forehead). Two signals, RightSignal-Central Reference and LeftSignal-CentralReference, are passed to the ADS1294 chip, averaged, and used to provide the signal for the DRL to compensate. However, the present application describes a recording device that routes the DRL signal to a conductive silicon sheet that surrounds all three electrodes, either as one continuous sheet of silicon or as discrete, electrically connected silicon surrounds for each electrode, enabling balanced and simultaneous noise compensation for each electrode. In prior designs in which the DRL is not evenly distributed across electrodes, the circuit tends to oscillate, likely due to imbalances in the DRL compensation and feedback cycling. For example, a 5-electrode design which consists of the same 3 recording electrodes described above (RightSignal, CentralReference, and LeftSignal) with the DRL signal split and placed only on either side of the CentralReference tends to oscillate, likely due to overcompensation at the CentralReference relative to the other two electrodes. The voltage signals as measured by the multichannel voltage recording device can be applied to display virtual objects generated using, for example, an augmented reality application.

Augmented reality applications allow a user to experience information, such as in the form of a three-dimensional virtual object displayed in a transparent lens or in a non-transparent display. In the case of a non-transparent display, the virtual object is displayed as an overlay on a picture of a physical object captured by a camera of a device. The physical object may include a visual reference that the augmented reality application can identify. The three-dimensional virtual object may be selected based on the recognized visual reference or a state of the user. A rendering of the visualization of the three-dimensional virtual object may be based on a position of the display relative to the visual reference. The virtual object may change based on a state of a user. For example, if a real-time algorithm identifies that the user is fixing his/her gaze, the display device may display a first virtual object. If the real-time algorithm identifies that the user is looking around, the display device may display a second virtual object different from the first virtual object.

In another example embodiment, the device includes a camera configured to capture a reference identifier from a physical object. The augmented reality application identifies a virtual object associated with the reference identifier, displays the virtual object in a display of the device, in response to a relative movement between the device and the physical object caused by a user, and modifies the virtual object based on the real-time state or activity of a user of the device. The real-time application identifies a change in the state or activity of a user of the device. The augmented reality application modifies the virtual object based on the change in the state or activity of the user of the device.

In another example embodiment, the augmented reality application communicates the reference identifier via a network to a remote server. The remote server includes virtual object data associated with the reference identifier. The augmented reality application receives the virtual object data at the device, and displays the virtual image in the display using the virtual object data. In response to a relative movement between the device and the physical object caused by a user, the augmented reality application modifies the virtual image. The brain activity application receives brain or behavioral activity data of the user and changes a state of the virtual object in the virtual landscape based on the brain, behavioral, or physical activity data.

In another example embodiment, a non-transitory machine-readable storage device may store a set of instructions that, when executed by at least one processor, causes the at least one processor to perform the method operations discussed within the present disclosure.

Certain example embodiments are described herein as including modules. Modules may constitute software modules (e.g., code stored or otherwise embodied in a machine-readable medium or in a transmission medium), hardware modules, or any suitable combination thereof. A "hardware module" is a tangible (e.g., non-transitory) physical component (e.g., a set of one or more processors) capable of performing certain operations and may be configured or arranged in a certain physical manner. In various example embodiments, one or more computer systems or one or more hardware modules thereof may be configured by software (e.g., an application or portion thereof) as a hardware module that operates to perform operations described herein for that module.

In some example embodiments, a hardware module may be implemented mechanically, electronically, hydraulically, or any suitable combination thereof. For example, a hardware module may include dedicated circuitry or logic that is permanently configured to perform certain operations. A hardware module may be or include a special-purpose processor, such as a field programmable gate array (FPGA) or an ASIC. A hardware module may also include programmable logic or circuitry that is temporarily configured by software to perform certain operations. As an example, a hardware module may include software encompassed within a CPU or other programmable processor. It will be appreciated that the decision to implement a hardware module mechanically, hydraulically, in dedicated and permanently configured circuitry, or in temporarily configured circuitry (e.g., configured by software) may be driven by cost and time considerations.

Accordingly, the phrase "hardware module" should be understood to encompass a tangible entity that may be physically constructed, permanently configured (e.g., hard-wired), or temporarily configured (e.g., programmed) to operate in a certain manner or to perform certain operations described herein. Furthermore, as used herein, the phrase "hardware-implemented module" refers to a hardware module. Considering example embodiments in which hardware modules are temporarily configured (e.g., programmed), each of the hardware modules need not be configured or instantiated at any one instance in time. For example, where a hardware module includes a CPU configured by software to become a special-purpose processor, the CPU may be configured as respectively different special-purpose processors (e.g., each included in a different hardware module) at different times. Software (e.g., a software module) may accordingly configure one or more processors, for example, to become or otherwise constitute a particular hardware module at one instance of time and to become or otherwise constitute a different hardware module at a different instance of time.

Hardware modules can provide information to, and receive information from, other hardware modules. Accordingly, the described hardware modules may be regarded as being communicatively coupled. Where multiple hardware modules exist contemporaneously, communications may be achieved through signal transmission (e.g., over suitable circuits and buses) between or among two or more of the hardware modules. In embodiments in which multiple hardware modules are configured or instantiated at different times, communications between such hardware modules may be achieved, for example, through the storage and retrieval of information in memory structures to which the multiple hardware modules have access. For example, one hardware module may perform an operation and store the output of that operation in a memory (e.g., a memory device) to which it is communicatively coupled. A further hardware module may then, at a later time, access the memory to retrieve and process the stored output. Hardware modules may also initiate communications with input or output devices, and can operate on a resource (e.g., a collection of information from a computing resource).

The various operations of example methods described herein may be performed, at least partially, by one or more processors that are temporarily configured (e.g., by software) or permanently configured to perform the relevant operations. Whether temporarily or permanently configured, such processors may constitute processor-implemented modules that operate to perform one or more operations or functions described herein. As used herein, "processor-implemented module" refers to a hardware module in which the hardware includes one or more processors. Accordingly, the operations described herein may be at least partially processor-implemented, hardware-implemented, or both, since a processor is an example of hardware, and at least some operations within any one or more of the methods discussed herein may be performed by one or more processor-implemented modules, hardware-implemented modules, or any suitable combination thereof.

Moreover, such one or more processors may perform operations in a "cloud computing" environment or as a service (e.g., within a "software as a service" (SaaS) implementation). For example, at least some operations within any one or more of the methods discussed herein may be performed by a group of computers (e.g., as examples of machines that include processors), with these operations being accessible via a network (e.g., the Internet) and via one or more appropriate interfaces (e.g., an application program interface (API)). The performance of certain operations may be distributed among the one or more processors, whether residing only within a single machine or deployed across a number of machines. In some example embodiments, the one or more processors or hardware modules (e.g., processor-implemented modules) may be located in a single geographic location (e.g., within a home environment, an office environment, or a server farm). In other example embodiments, the one or more processors or hardware modules may be distributed across a number of geographic locations.

Throughout this specification, plural instances may implement components, operations, or structures described as a single instance. Although individual operations of one or more methods are illustrated and described as separate operations, one or more of the individual operations may be performed concurrently, and nothing requires that the operations be performed in the order illustrated. Structures and their functionality presented as separate components and functions in example configurations may be implemented as a combined structure or component with combined functions. Similarly, structures and functionality presented as a single component may be implemented as separate components and functions. These and other variations, modifications, additions, and improvements fall within the scope of the subject matter herein.

Some portions of the subject matter discussed herein may be presented in terms of algorithms or symbolic representations of operations on data stored as bits or binary digital signals within a memory (e.g., a computer memory or other machine memory). Such algorithms or symbolic representations are examples of techniques used by those of ordinary skill in the data processing arts to convey the substance of their work to others skilled in the art. As used herein, an "algorithm" is a self-consistent sequence of operations or similar processing leading to a desired result. In this context, algorithms and operations involve physical manipulation of physical quantities. Typically, but not necessarily, such quantities may take the form of electrical, magnetic, or optical signals capable of being stored, accessed, transferred, combined, compared, or otherwise manipulated by a machine. It is convenient at times, principally for reasons of common usage, to refer to such signals using words such as "data," "content," "bits," "values," "elements," "symbols," "characters," "terms," "numbers," "numerals," or the like. These words, however, are merely convenient labels and are to be associated with appropriate physical quantities.

Unless specifically stated otherwise, discussions herein using words such as "accessing," "processing," "detecting," "computing," "calculating," "determining," "generating," "presenting," "displaying," or the like refer to actions or processes performable by a machine (e.g., a computer) that manipulates or transforms data represented as physical (e.g., electronic, magnetic, or optical) quantities within one or more memories (e.g., volatile memory, non-volatile memory, or any suitable combination thereof), registers, or other machine components that receive, store, transmit, or display information. Furthermore, unless specifically stated otherwise, the terms "a" or "an" are herein used, as is common in patent documents, to include one or more than one instance. Finally, as used herein, the conjunction "or" refers to a non-exclusive "or," unless specifically stated otherwise.

The following embodiments describe various example embodiments of methods, machine-readable media, and systems (e.g., machines, devices, or other apparatus) discussed herein.

DRAWINGS

FIG. 1 is a block diagram illustrating an example of a network environment suitable for a multichannel voltage recording device, according to some example embodiments.

A network environment 100 includes a multichannel voltage recording device 114, a display device 102, and a server 106, communicatively coupled to each other via a network 104. The display device 102 and the server 106 may each be implemented in a computer system, in whole or in part, as described below with respect to FIG. 11.

Figure 2:
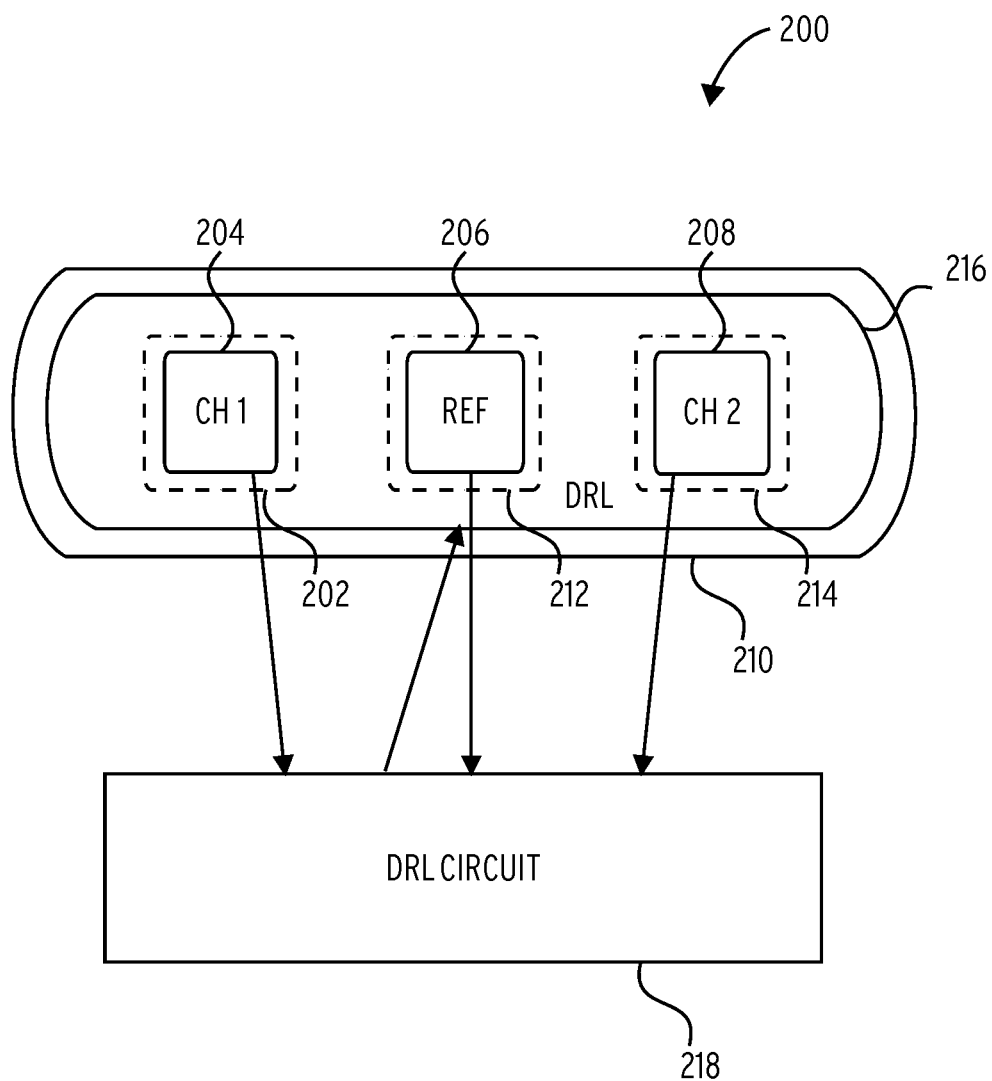
FIG. 2 illustrates an example embodiment of a multichannel voltage recording device.

The server 106 may be part of a network-based system. For example, the network-based system may be or include a cloud-based server system that provides augmented or additional information, such as virtual objects (e.g., 3D models), to the display device 102 based on the voltage signals recorded by the multichannel voltage recording device 114. Sensors of the multichannel voltage recording device 114 are connected to the skin of the user 110 to measure the voltage signals from the user 110. Examples of the multichannel voltage recording device 114 are illustrated in FIG. 2.

A user 110 may use the display device 102 and look at a physical object 112 in a real world physical environment. The user 110 of the display device 102 may be a human user (e.g., a human being), a machine user (e.g., a computer configured by a software program to interact with the display device 102), or any suitable combination thereof (e.g., a human assisted by a machine or a machine supervised by a human). The user 110 is not part of the network environment 100, but is associated with the display device 102. For example, the display device 102 may be a computing device with a camera and a display such as a tablet, smartphone, or a wearable computing device (e.g., helmet or glasses). In another example embodiment, the computing device may be hand held or may be removably mounted to the head of the user 110. In one example, the display may be a screen that displays what is captured with a camera of the display device 102. In another example, the display of the display device 102 may be transparent or partially transparent such as in lenses of wearable computing glasses or the visor or a face shield of a helmet.

The user 110 may be a user of a multichannel voltage recording application and an AR application in the display device 102 and at the server 106. The multichannel voltage recording application determines a state of the user 110 based on biometric signals of the user 110. The state may be for example, a mental state of mind (e.g., happy, sad) or a physical state (e.g., relaxed, tensed). The AR application may provide the user 110 with a display of virtual objects triggered by identified objects (e.g., physical object 112) in the physical environment and based on the state of the user 110. For example, the physical object 112 include identifiable objects such as a 2D physical object (e.g., a picture), a 3D physical object (e.g., a factory machine), a location (e.g., at the bottom floor of a factory), or any references (e.g., perceived corners of walls or furniture, geometric shape and pattern of an apple) in the real world physical environment. The AR application may include computer vision recognition to determine corners, objects, lines, letters, and so forth.

The multichannel voltage recording device 114 may be connected to the head of the user 110 or the skin on other body parts of the user 110. The multichannel voltage recording device 114 may be external to the display device 102 or part of the display device 102. For example, the display device 102 may be a helmet with a visor with the multichannel voltage recording device 114 (e.g., electrodes) disposed inside the helmet. The AR application in the display device 102 may generate or change virtual content based on a real-time analysis of data from the multichannel voltage recording device 114.

In one example embodiment, the objects in the image are tracked and recognized locally in the display device 102 using a local context recognition dataset or any other previously stored dataset of the AR application of the display device 102. The local context recognition dataset may include a library of virtual objects associated with real-world physical objects or references. In one example, the display device 102 identifies feature points in an image of the physical object 112. The display device 102 may also identify tracking data related to the physical object 112 (e.g., GPS location of the display device 102, orientation, distance to the physical object 112). If the captured image is not recognized locally at the display device 102, the display device 102 can download additional information (e.g., 3D model or other augmented data) corresponding to the captured image, from a database of the server 106 over the network 104.

In another example embodiment, the physical object 112 in the image is tracked and recognized remotely at the server 106 using a remote context recognition dataset or any other previously stored dataset of an AR application in the server 106. The remote context recognition dataset module may include a library of virtual objects or augmented information associated with real-world physical objects or references.

External sensors 108 may be associated with, coupled to, related to the physical object 112 to measure a location, status, and characteristics of the physical object 112. Examples of measured readings may include and but are not limited to weight, pressure, temperature, velocity, direction, position, intrinsic and extrinsic properties, acceleration, and dimensions. For example, external sensors 108 may be disposed throughout a factory floor to measure movement, pressure, orientation, and temperature. The external sensors 108 can also be used to measure a location, status, and characteristics of the display device 102 and the user 110. The server 106 can compute readings from data generated by the external sensors 108. The server 106 can generate virtual indicators such as vectors or colors based on data from external sensors 108. Virtual indicators are then overlaid on top of a live image or a view of the physical object 112 in a line of sight of the user 110 to show data related to the object. For example, the virtual indicators may include arrows with shapes and colors that change based on real-time data. The visualization may be provided to the physical object 112 so that the display device 102 can render the virtual indicators in a display of the display device 102. In another example embodiment, the virtual indicators are rendered at the server 106 and streamed to the display device 102.

The external sensors 108 may include other sensors used to track the location, movement, and orientation of the display device 102 externally without having to rely on sensors internal to the display device 102. The sensors 112 may include optical sensors (e.g., depth-enabled 3D camera), wireless sensors (Bluetooth, Wi-Fi), GPS sensors, and audio sensors to determine the location of the user 110 wearing the display device 102, distance of the user 110 to the external sensors 108 (e.g., sensors placed in corners of a venue or a room), the orientation of the display device 102 to track what the user 110 is looking at (e.g., direction at which the display device 102 is pointed, e.g., display device 102 pointed towards a player on a tennis court, display device 102 pointed at a person in a room).

In another example embodiment, data from the external sensors 108 and internal sensors in the display device 102 may be used for analytics data processing at the server 106 (or another server) for analysis on usage and how the user 110 is interacting with the physical object 112 in the physical environment. Live data from other servers may also be used in the analytics data processing. For example, the analytics data may track at what locations (e.g., points or features) on the physical or virtual object the user 110 has looked, how long the user 110 has looked at each location on the physical or virtual object, how the user 110 wore the display device 102 when looking at the physical or virtual object, which features of the virtual object the user 110 interacted with (e.g., such as whether the user 110 engaged with the virtual object), and any suitable combination thereof. The display device 102 receives a visualization content dataset related to the analytics data. The display device 102 then generates a virtual object with additional or visualization features, or a new experience, based on the visualization content dataset.

Any of the machines, databases, or devices shown in FIG. 1 may be implemented in a general-purpose computer modified (e.g., configured or programmed) by software to be a special-purpose computer to perform one or more of the functions described herein for that machine, database, or device. For example, a computer system able to implement any one or more of the methodologies described herein is discussed below with respect to FIG. 11. As used herein, a "database" is a data storage resource and may store data structured as a text file, a table, a spreadsheet, a relational database (e.g., an object-relational database), a triple store, a hierarchical data store, or any suitable combination thereof. Moreover, any two or more of the machines, databases, or devices illustrated in FIG. 1 may be combined into a single machine, and the functions described herein for any single machine, database, or device may be subdivided among multiple machines, databases, or devices.

The network 104 may be any network that enables communication between or among machines (e.g., server 106), databases, and devices (e.g., device 101). Accordingly, the network 104 may be a wired network, a wireless network (e.g., a mobile or cellular network), or any suitable combination thereof. The network 104 may include one or more portions that constitute a private network, a public network (e.g., the Internet), or any suitable combination thereof.

FIG. 2 illustrates an example embodiment of a multichannel voltage sensor 200. The multichannel voltage sensor 200 includes electrodes 204, 206, 208, a conductive material 216, a border insulator 210, an electrode insulator 202, and a DRL circuit 218. A close juxtaposition (e.g., distance between electrodes is less than 50 mm) of the electrodes 204, 206, and 208 generally results in oscillatory activities due to imbalance in the DRL circuit 218 and thus more noise.

The multichannel voltage sensor 200 allows for a small form factor device to be used for simultaneous low-noise sampling from multiple adjacent areas in the brain or other electrically active organ, such as the heart or gastronemius. Voltage recordings are made through at least three electrodes 204, 206, and 208. For example, electrode 204 corresponds to RightSignal, electrode 206 corresponds to CentralReference, and electrode 208 corresponds to LeftSignal. Electrodes 204, 206, and 208 are evenly spaced across the forehead of the user 110. These signals are passed to the DRL circuit 218 (e.g., ADS1294 chip from Texas Instruments), averaged, and used to provide the DRL signal for the DRL circuit 218 to compensate.

The DRL circuit 218 provides the DRL signal to a conductive material 216 (e.g., conductive silicon sheet or any other types of conductive material) that surrounds all three electrodes 204, 206, 208, enabling balanced and simultaneous noise compensation. The conductive material can be either a sheet or discrete units that surround each recording electrode, as long as the discrete units are electrically connected and surround each recording electrode equally. In contrast, the DRL signal is not evenly distributed across electrodes in prior voltage sensors. As a result, the circuit tends to oscillate, likely due to imbalances in the DRL compensation and feedback cycling. For example, a five electrode design which consists of the same three recording electrodes described above (RightSignal, CentralReference, and LeftSignal) with the DRL signal split and placed only on either side of the CentralReference tends to oscillate, likely due to overcompensation at the CentralReference relative to the other two electrodes.

An electrode insulator surrounds each electrode to insulate each electrode from the conductive material 216. For example, an electrode insulator 202 surrounds electrode 204. An electrode insulator 212 surrounds electrode 206. An electrode insulator 214 surrounds electrode 208. In one example, the electrode insulator may be a few millimeter thick (1 mm to 2 mm).

In other example embodiments, the multichannel voltage sensor 200 enables high quality recording from adjacent areas using a palm-sized device and allows the monitoring and detection of activity differences and similarities in the two brain hemispheres. Hemispheric asymmetry is known to correlate with certain behavioral states, such as stress, and with certain pathological conditions, such as schizophrenia and depression. Thus, this multichannel voltage sensor 200 could be used to accurately detect stress or, potentially, diagnose mental illness. It could also be used to monitor facial movements. Other possible applications include the detection of certain heart abnormalities and zones of skeletal muscle weakness.

Figure 3:
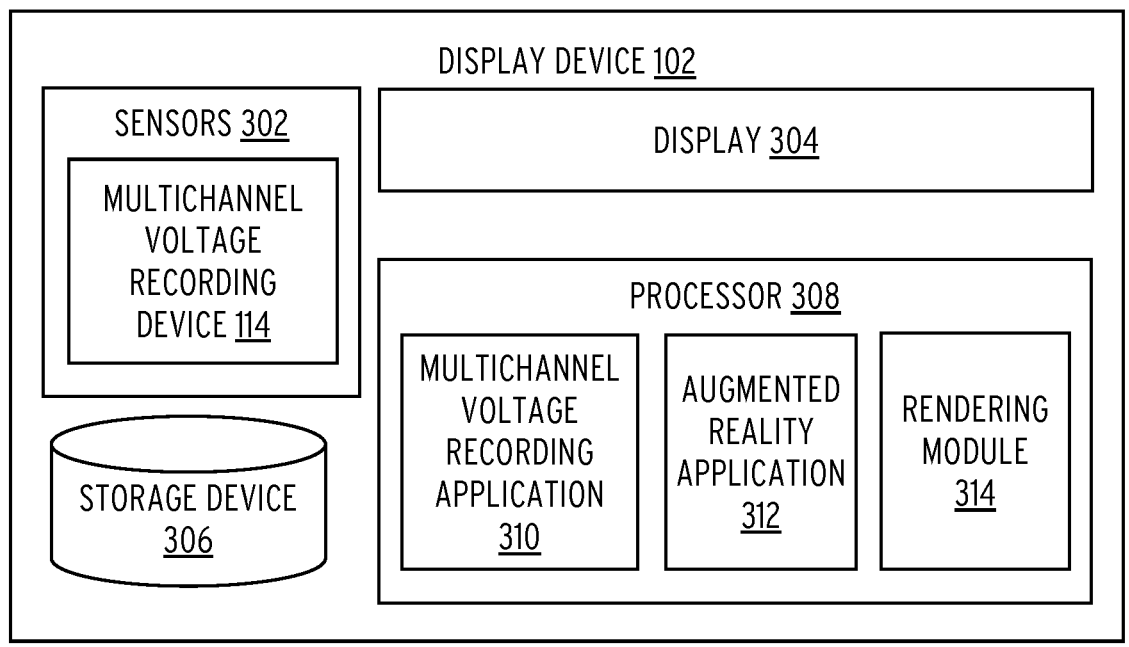
FIG. 3 is a block diagram illustrating an example embodiment of modules (e.g., components) of a display device suitable for recording biometric data and generating augmented reality content based on the biometric data.

FIG. 3 is a block diagram illustrating an example embodiment of modules (e.g., components) of a display device suitable for recording biometric data and generating augmented reality content based on the biometric data.

The display device 102 includes sensors 302, a display 304, a processor 308, and a storage device 306. For example, the display device 102 may include a mobile computing device (e.g., a smartphone, a tablet, a laptop) or a wearable computing device (e.g., a smart helmet, a smart visor, a smart watch or any other computing device worn by the user 110).

In one example embodiment, the sensors 302 may include the multichannel voltage recording device 114 (e.g., at least three electrodes) to measure electrical activity from a body of the user 110. FIG. 3 illustrates an example of the multichannel voltage recording device 114. For example, the multichannel voltage recording device 114 may include at least three electrodes connected to the user 110 (e.g., forehead or other body parts). The multichannel voltage recording device 114 may be used to measure EEG (electroencephalography) waves of brains, EMG (electromyography) waves of muscles, ECG (electrocardiography) waves of the heart, and EOG (electro-oculogram) waves of eyes. The multichannel voltage recording device 114 can also be used to monitor brainwaves through EEG by detecting electrical signals about the user's present state or activity. The multichannel voltage recording device 114 may be implemented, for example, by using a headset or a helmet worn by the user 110. In another example, the multichannel voltage recording device 114 can be used to monitor facial muscles to detect facial expressions of the user 110.

In another example embodiment, the sensors 302 may also include: an optical sensor (e.g., a charged-coupled device (CCD)), an orientation sensor (e.g., gyroscope), an audio sensor (e.g., a microphone), a thermometer, an infrared camera, a barometer, and/or a humidity sensor. For example, the display device 102 may include a front-facing camera for tracking eyes movement and facial expression of the user, and a rear-facing camera for capturing a picture or a video of a physical object (or another displayed virtual object). It is noted that the sensors 302 described herein are for illustration purposes and the sensors 302 are thus not limited to the one described. In another example, sensors 302 may not be physically connected to the display device 102 but are instead coupled to the display device 102 via wireless means such as Wi-Fi and Bluetooth®.

The display 304 includes, for example, a touchscreen display configured to receive a user input via a contact on the touchscreen display. In another example, the display 304 includes a screen or monitor configured to display images generated by the processor 308. In another embodiment, the display 304 may be a transparent, a translucent, or a see-through display.

The processor 308 includes a multichannel voltage recording application 310, an augmented reality application 312, and a rendering module 314. The multichannel voltage recording application 310 determines a state or activity (e.g., stressed, relaxed) of the user 110 in real-time based on outputs from the multichannel voltage recording device 114. The state or activity may be based on the intensity or pattern of the outputs of the multichannel voltage recording device 114. The state or activity may be classified in a spectrum where the state or activity may be predefined relative to the range of outputs from the multichannel voltage recording device 114. For example, a first output range may be categorized as relaxed and a second output range may be categorized as stressed.

In one example embodiment, the multichannel voltage recording application 310 identifies the intensity or pattern of the different types of electric waves recorded from the user 110 over a short period of time (a sampling period). The multichannel voltage recording application 310 receives voltage signals from the multichannel voltage recording device 114 to identify a state or activity of the user 110. In another example, the multichannel voltage recording application 310 may use the multichannel voltage recording device 114 (e.g., EEG electrodes) alone or in combination with other sensors from sensors 302 (e.g., microphone, camera, and heart rate monitor).

The augmented reality application 312 generates a display of a virtual object (three-dimensional or two-dimensional model) in the display 304. In another example, the augmented reality application 312 generates a display of the virtual object overlaid on an image of the physical object 112 captured by the sensors 302. The virtual object may be selected or generated based on the state or activity of the user as determined by the multichannel voltage recording application 310. The virtual object and features of the virtual object may be further manipulated based on a change in the state or activity of the user.

In another example embodiment, the augmented reality application 312 receives data from sensors 302 (e.g., receive an image of the physical object 112) and identifies and recognizes the physical object 112 using machine-vision recognition techniques. The augmented reality application 312 then retrieves from the storage device 306, AR content associated with the physical object 112. In one example embodiment, the augmented reality application 312 identifies a visual reference (e.g., a logo or QR code) on the physical object 112 (e.g., a chair) and tracks the location of the visual reference within the display 304 of the display device 102. The visual reference may also be referred to as a marker and may consist of an identifiable image, symbol, letter, number, machine-readable code. For example, the visual reference may include a bar code, a quick response (QR) code, or an image that has been previously associated with the virtual object.

The rendering module 314 renders virtual objects based on data from sensors 302. For example, the rendering module 314 renders a display of a virtual object (e.g., a door with a color based on the temperature inside the room as detected by sensors 302 based on a three-dimensional model of the virtual object (e.g., 3D model of a virtual door) associated with the physical object 112 (e.g., a physical door). In another example, the rendering module 314 generates a display of the virtual object overlaid on an image of the physical object 112 captured by a camera of the display device 102. The virtual object may be further manipulated (e.g., by the user 110) by moving the physical object 112 relative to the display device 102. Conversely, the display of the physical object 112 may be manipulated (e.g., by the user 110) by moving the display device 102 relative to the physical object 112.

In one example embodiment, the rendering module 314 identifies the physical object 112 (e.g., a physical telephone) based on data from sensors 302 and external sensors 108, accesses virtual functions (e.g., increase or lower the volume of a nearby television) associated with physical manipulations (e.g., lifting a physical telephone handset) of the physical object 112, and generates a virtual function corresponding to a physical manipulation of the physical object 112.

In another example embodiment, the rendering module 314 determines whether the captured image matches an image locally stored in the storage device 306 that includes a local database of images and corresponding additional information (e.g., three-dimensional model and interactive features). The rendering module 314 retrieves a primary content dataset from the server 106, generates and updates a contextual content dataset based on an image captured with the display device 102.

The storage device 306 stores data from the multichannel voltage recording device 114 and sensors 302, a database of visual references, virtual objects corresponding to the visual references, features of the virtual objects corresponding to the virtual objects, and corresponding states or activities. The features of the virtual objects can change with the state or activity of the user. For example, the color of the virtual chair can change from blue to red as the user becomes more stressed. The virtual chair may be displayed in a blue color if the user is relaxed.

The storage device 306 further includes a database of visual references (e.g., images, visual identifiers, features of images) and corresponding experiences (e.g., three-dimensional virtual objects, interactive features of the three-dimensional virtual objects). For example, the visual reference may include a machine-readable code or a previously identified image (e.g., a picture of a screwdriver). The previously identified image of the screwdriver may correspond to a three-dimensional virtual model of the screwdriver that can be viewed from different angles by manipulating the position of the display device 102 relative to the picture of the screwdriver. Features of the three-dimensional virtual screwdriver may include selectable icons on the three-dimensional virtual model of the screwdriver. An icon may be selected or activated using a user interface on the display device 102.

In another example embodiment, the storage device 306 includes a primary content dataset, a contextual content dataset, and a visualization content dataset. The primary content dataset includes, for example, a first set of images and corresponding experiences (e.g., interaction with three-dimensional virtual object models). For example, an image may be associated with one or more virtual object models. The primary content dataset may include a core set of images of the most popular images determined by the server 106. The core set of images may include a limited number of images identified by the server 106. For example, the core set of images may include the images depicting covers of the ten most popular machines and their corresponding experiences (e.g., virtual objects that represent the ten most popular physical objects viewed by the display device 102). In another example, the server 106 may generate the first set of images based on the most popular or often scanned images received at the server 106. Thus, the primary content dataset does not depend on objects or images scanned by the rendering module 314 of the display device 102.

The contextual content dataset includes, for example, a second set of images and corresponding experiences (e.g., three-dimensional virtual object models) retrieved from the server 106. For example, images captured with the display device 102 that are not recognized (e.g., by the server 106) in the primary content dataset are submitted to the server 106 for recognition. If the captured image is recognized by the server 106, a corresponding experience may be downloaded at the display device 102 and stored in the contextual content dataset. Thus, the contextual content dataset relies on the context in which the display device 102 has been used. As such, the contextual content dataset depends on objects or images scanned by the rendering module 314.

In one embodiment, the display device 102 may communicate over the network 102 with the server 106 to retrieve a portion of a database of visual references, corresponding three-dimensional virtual objects, and corresponding interactive features of the three-dimensional virtual objects. The network 102 may be any network that enables communication between or among machines, databases, and devices (e.g., the display device 102). Accordingly, the network 102 may be a wired network, a wireless network (e.g., a mobile or cellular network), or any suitable combination thereof. The network 104 may include one or more portions that constitute a private network, a public network (e.g., the Internet), or any suitable combination thereof.

Any one or more of the modules described herein may be implemented using hardware (e.g., a processor of a machine) or a combination of hardware and software. For example, any module described herein may configure a processor to perform the operations described herein for that module. Moreover, any two or more of these modules may be combined into a single module, and the functions described herein for a single module may be subdivided among multiple modules. Furthermore, according to various example embodiments, modules described herein as being implemented within a single machine, database, or device may be distributed across multiple machines, databases, or devices.

Figure 4:
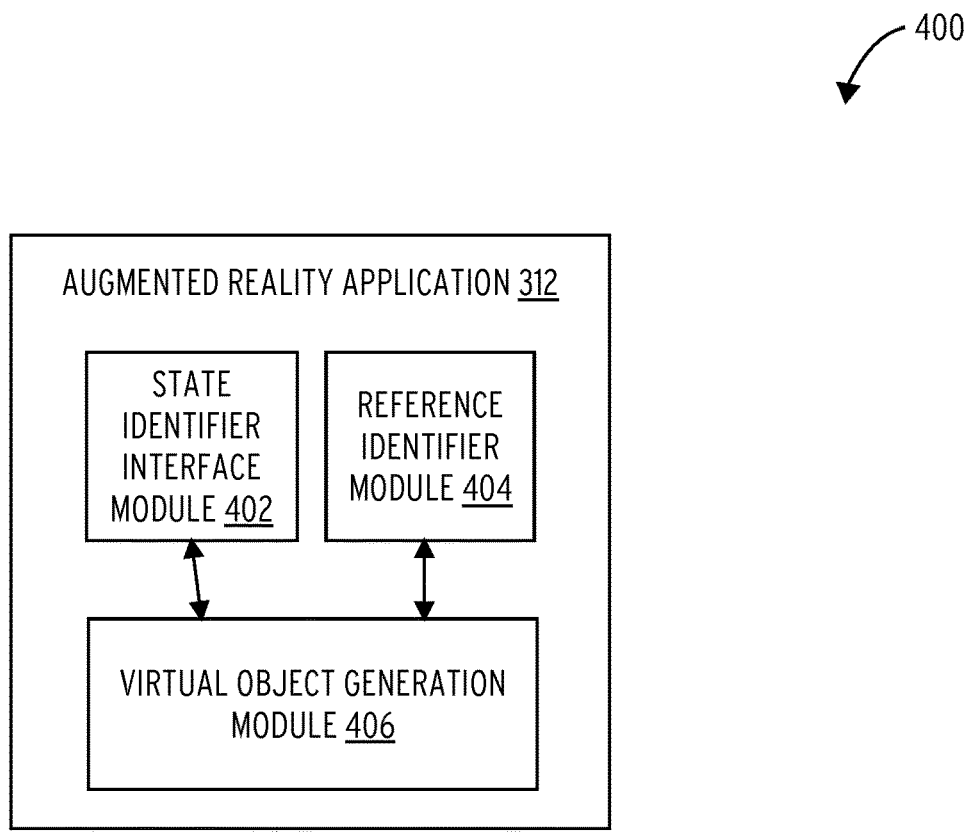
FIG. 4 is a block diagram illustrating an example embodiment of modules (e.g., components) of an augmented reality application.

FIG. 4 is a block diagram 400 illustrating an example embodiment of modules (e.g., components) of an augmented reality application. The augmented reality application 312 includes a state identifier interface module 402, a reference identifier module 404, and a virtual object generation module 406.

The state identifier interface module 402 identifies a computed state or activity of the user 110 based on the multichannel voltage recording application 310. For example, the multichannel voltage recording application 310 may indicate that the user is relaxed. The multichannel voltage recording application 310 may also identify that a change in the level of relaxation of the user.

The reference identifier module 404 identifies a visual reference on the physical object 112 captured by sensors 302 (and optionally external sensors 108). For example, a camera of the display device 102 captures an image of the physical object 112, such as a page on a newspaper. The page on the newspaper may include an article and a picture. The picture may have been already identified as a visual reference in the storage device 306. The picture may be associated with a corresponding three-dimensional model of an object (e.g., a virtual sofa).

The virtual object generation module 406 generates and displays a visualization of a three-dimensional virtual object engaged with an image of the physical object captured by the sensors 302 of the display device 102 (e.g., the virtual sofa floats and rotates on top of the magazine page). The virtual object may be based on the visual reference (e.g., a furniture ad in the magazine page). In one embodiment, each virtual object may be uniquely associated with a visual reference. The virtual object generation module 406 renders the visualization of the virtual object based a position of the display device 102 relative to the visual reference. In another example embodiment, attributes of the virtual object may be based on the state or activity of the user 110. For example, the virtual object generation module 406 may generate a 3D model of a virtual blue color sofa when the state identifier interface module 402 indicates that the user is relaxed. Similarly, the virtual object generation module 406 may generate a 3D model of a red color sofa when the state identifier interface module 402 indicates that the user 110 is stressed.

In yet another example embodiment, the virtual object generation module 406 generates a virtual object based on a change in the level of relaxation of the user 110. For example, a blue color car may morph into a red color sofa when the state of mind of the user 110 indicates that the user 110 is getting stressed.

Figure 5:
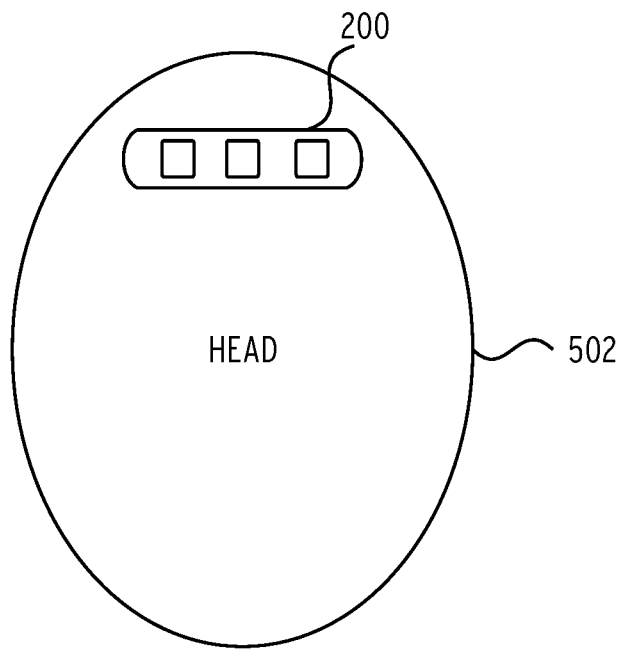
FIG. 5 is a diagram illustrating a top view of a head of a user with a multichannel voltage recording device applied to the head of the user.

FIG. 5 is a diagram illustrating a top view of a head of a user with the multichannel voltage sensor 200 applied to the head 502 (e.g., forehead) of the user.

Figure 6:
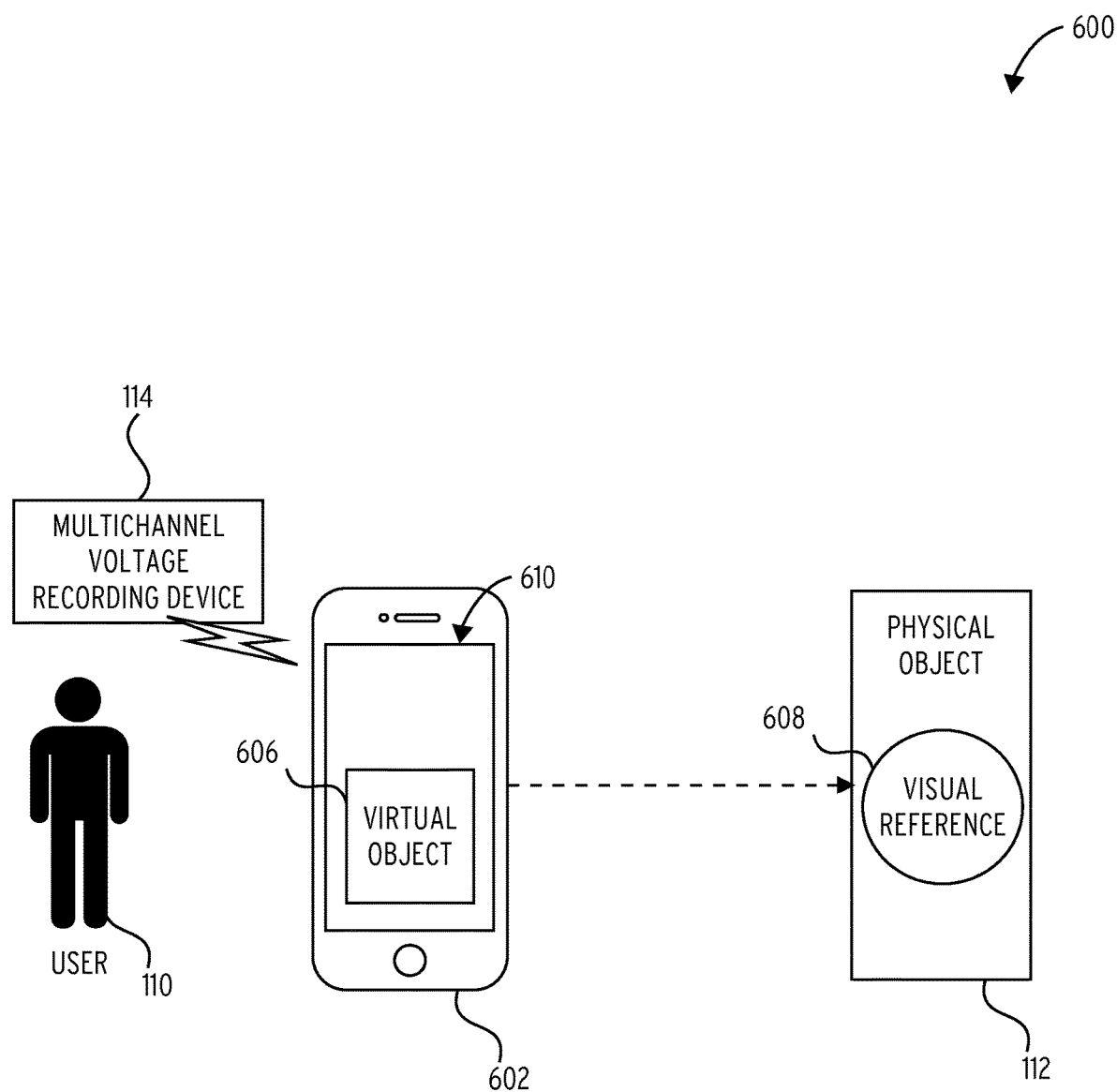
FIG. 6 is a diagram illustrating an example operation of a display device suitable for generating augmented reality content based on biometric data measured by a multichannel voltage recording device, according to some example embodiments.

FIG. 6 is a diagram 600 illustrating an example operation of a display device suitable for generating augmented reality content based on biometric data measured by a multichannel voltage recording device, according to some example embodiments.

The user 110 is equipped with the multichannel voltage recording device 114 connected to the forehead (or other body parts) of the user 110. As previously described, multichannel voltage recording device 114 includes other types of measuring devices for measuring skin temperature and heart rate activity among others. The electrodes may be physically coupled via wires to a mobile device 602 (e.g., smart phone) or a wearable display device (e.g., visor, eyeglasses, helmet). In another example, electrodes may communicate with the mobile device 602 wirelessly using wireless communication means (e.g., Wifi, Bluetooth®, ZigBee®).

The user 110 points a rear camera (not shown) of the mobile device 602 towards the physical object 112 having a visual reference 608 (e.g., uniquely identifiable visual pattern or features). As previously described, the visual reference 608 may include a picture, a machine-readable code, or any other identifier unique to the augmented reality application 312 in the mobile device 602. The physical object 112 may be, for example, a page of a magazine or newspaper. In another embodiment, the physical object 112 and the visual reference 608 may be combined together (e.g., a poster or a cup). In such case, the three-dimensional physical object may be used as a visual reference. For example, a three-dimensional object such as a cup having a specific pattern or design may be used as a visual reference. The mobile device 602 captures an image or a picture of the physical object 112 and the visual reference 608 using the rear camera.

The mobile device 602 displays a virtual object 606 in a display 610 of the mobile device 602 based on the visual reference 608 and voltage outputs as determined by the multichannel voltage recording device 114. For example, the mobile device 602 determines that the user 110 is geographically located at a particular office. The mobile device 602 determines from the multichannel voltage recording device 114 that the level of stress of the user 110 corresponds to a stressed state (as opposed to a relaxed state). In another embodiment, a front facing camera (not shown) of the mobile device 602 may further enhance and provide additional data on the state of mind of the user 110. For example, the mobile device 602 may obtain a live picture of the user 110 using the front facing camera to determine a smile or a frown. In another example, the front facing camera may be used for facial recognition to determine the identity of the user 110. The mobile device 602 may retrieve preferences from the user 110 such as, for example, favorite colors or items from a user profile (stored in the mobile device 602, or in a server of a social network service provider). In another example, the mobile device 602 determines, identifies, and manipulates the virtual object 606 to be displayed in the display based on a combination of the geographic location of the mobile device 602 (e.g., office, home, restaurant, city, country), time of capture (e.g., morning, afternoon, evening, holiday, weekend) of the visual reference 608, orientation (e.g., portrait or landscape, how close) of the mobile device 602 relative to the visual reference 608, identification of the user 110 (e.g., using facial recognition, or login information), preferences of the user 110 (e.g., favorite color, favorite type of music) social network information (e.g., number of friends, interests, proximity of friends, postings) related to the user 110, outputs from the multichannel voltage recording device 114 (e.g., EEG brain waves, EMG muscles waves, EOG eye movements, heart rate, blood pressure), and the visual reference 608.

The mobile device 602 may then display the virtual object 606 as an overlay on top of a picture of the physical object 112 based on the real-time state or activity the user 110. For example, the virtual object 606 may be a three-dimensional model of a building rendered on top of an image of the physical object 112 in the display 610 if the user 110's state of mind is identified as in a stressed state. In another example, if the user's state of mind determined to be relaxed, the mobile device 602 may generate a three-dimensional model of a vacation home rendered on top of the image of the physical object 112 in the display 610 of the mobile device 602. Thus, the mobile device 602 identifies which virtual object to display in response to the visual reference 608 and the present state or activity of the user 110.

Figure 7:
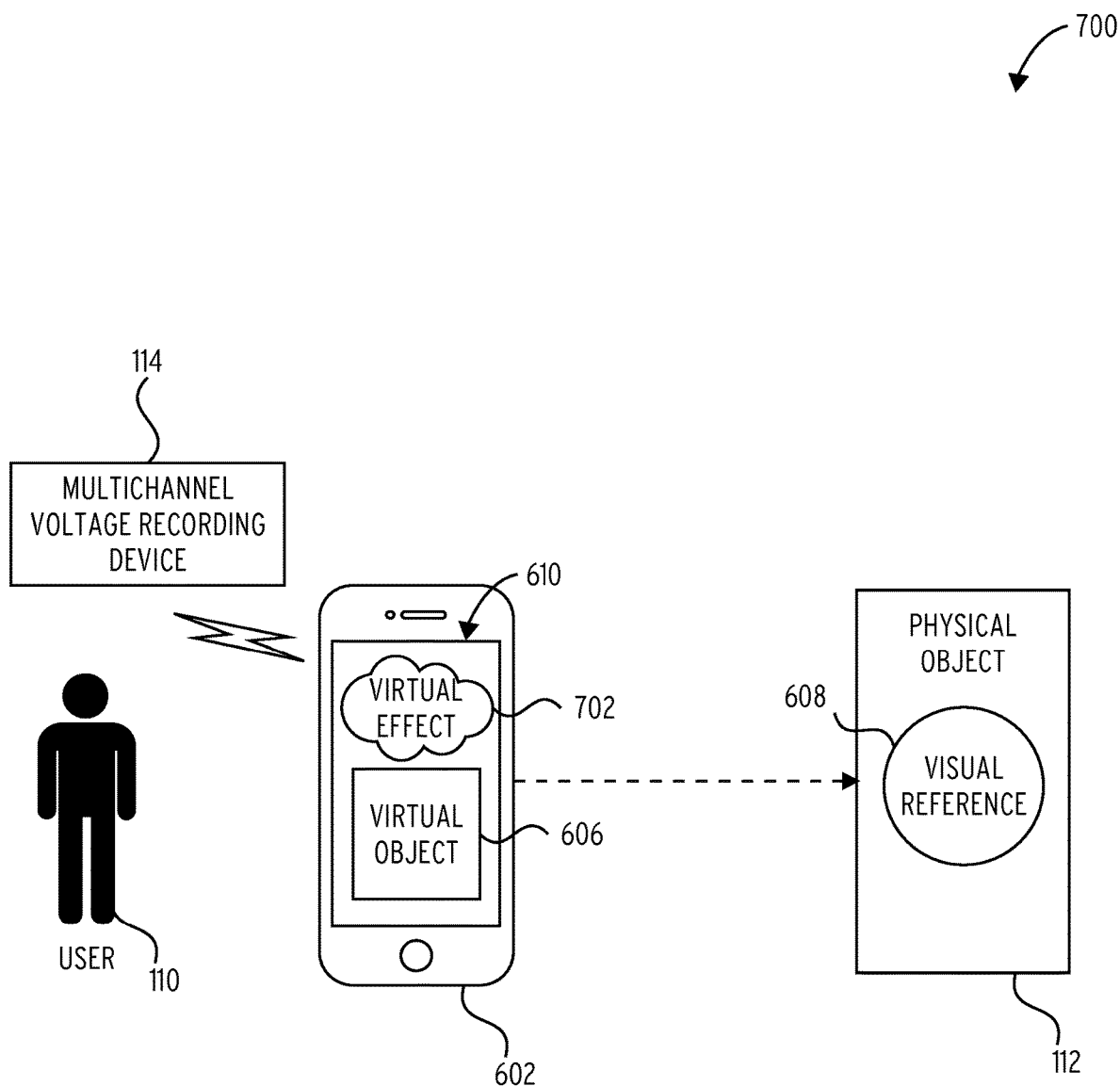
FIG. 7 is a diagram illustrating an example operation of a display device suitable for generating augmented reality content based on biometric data measured by a multichannel voltage recording device, according to some example embodiments.

FIG. 7 is a diagram 700 illustrating an example operation of a display device suitable for generating augmented reality content based on biometric data measured by a multichannel voltage recording device, according to some example embodiments.

The mobile device 602 determines a change in the state of mind of the user 110 (e.g., from focused to distracted, or from relaxed to stressed) or a change in physical state of the user 110 (e.g., change in heart beat rate). The mobile device 602 then generates a change to the virtual object 606 in the display 610 of the mobile device 602 based on the change in the state or activity of the user 110 in response to changes in outputs from the multichannel voltage recording device 114 and the front facing camera of the mobile device 602. For example, virtual effect 702 (e.g., dynamic animation of rain) may be displayed over the virtual object 606 in the display 610 when the mobile device 602 detects that the user 110 has frowned, stressed, or has a heart rate exceeding a threshold.

As such, changes of the already displayed virtual object 606 in the display 610 are determined based on the changes in the state of mind of the user 110. In another example, the color of the virtual object 606 may change to a lighter hue when the user 110 becomes more relaxed while looking at the virtual object 606. In another example, the texture of the virtual object 606 may change to a rougher texture when the state of mind of the user 110 indicates that the user 110 is agitated.

In another example embodiment, the mobile device includes a transparent display (not shown). The transparent display may be mounted to a head of the user (e.g., via eyeglass mount or headgear mount). In another example, the transparent display may be a handheld device that the user 110 holds and looks through to see the physical object 112 located behind the transparent display. The rear facing camera of the mobile device 602 may recognize physical objects being looked by the user (e.g., by comparing an image of the physical object 112 with a reference image). In particular, the position and orientation of the transparent display with respect to the user 110 and the physical object 112 may be used to determine a line of sight of the user 110. Using the determined line of the sight of the user 110, the mobile device 602 can identify in real time which physical objects are being looked and in particular which part of the physical object the user 110 is looking.

Once the mobile device 602 identifies that the recognized physical object 112 or the part of the recognized physical object 112 corresponds to a preidentified physical object or pre-identified part of the physical object 112, the mobile device 602 may trigger a corresponding action (e.g., sending an email, generating a sound, etc.) based on the state of mind of the user 110. For example, the mobile device 602 detects the user 110 is looking through the transparent display towards a bottom portion of a television set. The mobile device 602 recognizes the television set and determines that the bottom portion of the television set (being looked at by the user 110) is associated with an action corresponding to generating a communication to the television set to switch the TV on or off. If the user 110 has looked at the bottom portion of the television set for at least several seconds and the state of mind indicates that the user is relaxed, the mobile device 602 generates a corresponding signal to turn on or off the television set.

In another example, the mobile device 602 may display a virtual menu of TV channels overlaid on the physical TV set based on the state of mind of the user 110. For example, if the user 110 is excited, the virtual menu of TV channels may include sports channels and action movies. If the state of mind of the user 110 corresponds to a relaxed state, the virtual menu of TV channels may include news or music videos channels.

In another example, the user 110 may look through a transparent display of the mobile device 602 to a radio device. Similarly, a virtual menu of music channels may be displayed as a layer over the radio device based on the state of mind of the user 110. For example, the mobile device 602 displays a virtual menu showing classical or relaxing music channels when the multichannel voltage recording device 114 indicates that the user 110 is relaxed or sleepy. The state of mind of the user 110 may be computed in real-time using the multichannel voltage recording application 310.

Figure 8:
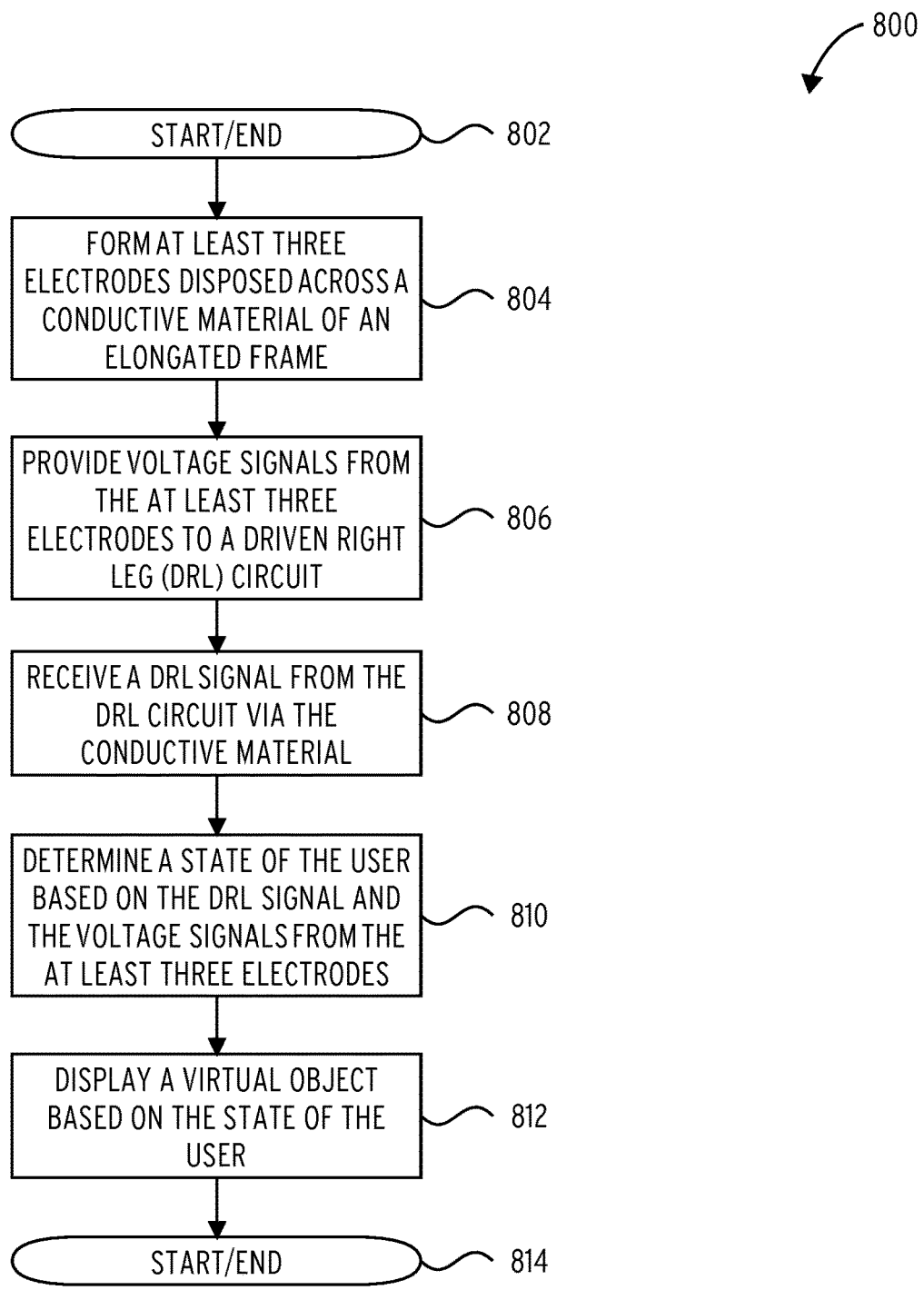
FIG. 8 is a flow diagram of a method for generating augmented reality content based on an analysis of biometric data from a multichannel voltage recording device, according to some example embodiments.

FIG. 8 is a flow diagram of a method 800 for generating augmented reality content based on an analysis of biometric data from a multichannel voltage recording device, according to some example embodiments. The method 800 can start at block 802.

At block 804, at least three electrodes are disposed across the conductive material 216 on an elongated frame. The electrodes are coupled and in contact with the skin of a user of the multichannel voltage recording device.

At block 806, the voltage signals from the at least three electrodes is provided to a driven right leg (DRL) circuit.

At block 808, the conductive material 216 receive a DRL signal from the DRL circuit. The DRL signal is based on the voltage signals from the at least three electrodes.

At block 810, the display device 102 determines a (mental or physical) state of the user based on the voltage signals from the at least three electrodes that are higher quality given the common mode compensation provided by the DRL circuit.

At block 812, the display device 102 displays a virtual object based on the (mental or physical) state of the user or a change in the state of the user. The method 800 can end at block 814.

Figure 9:
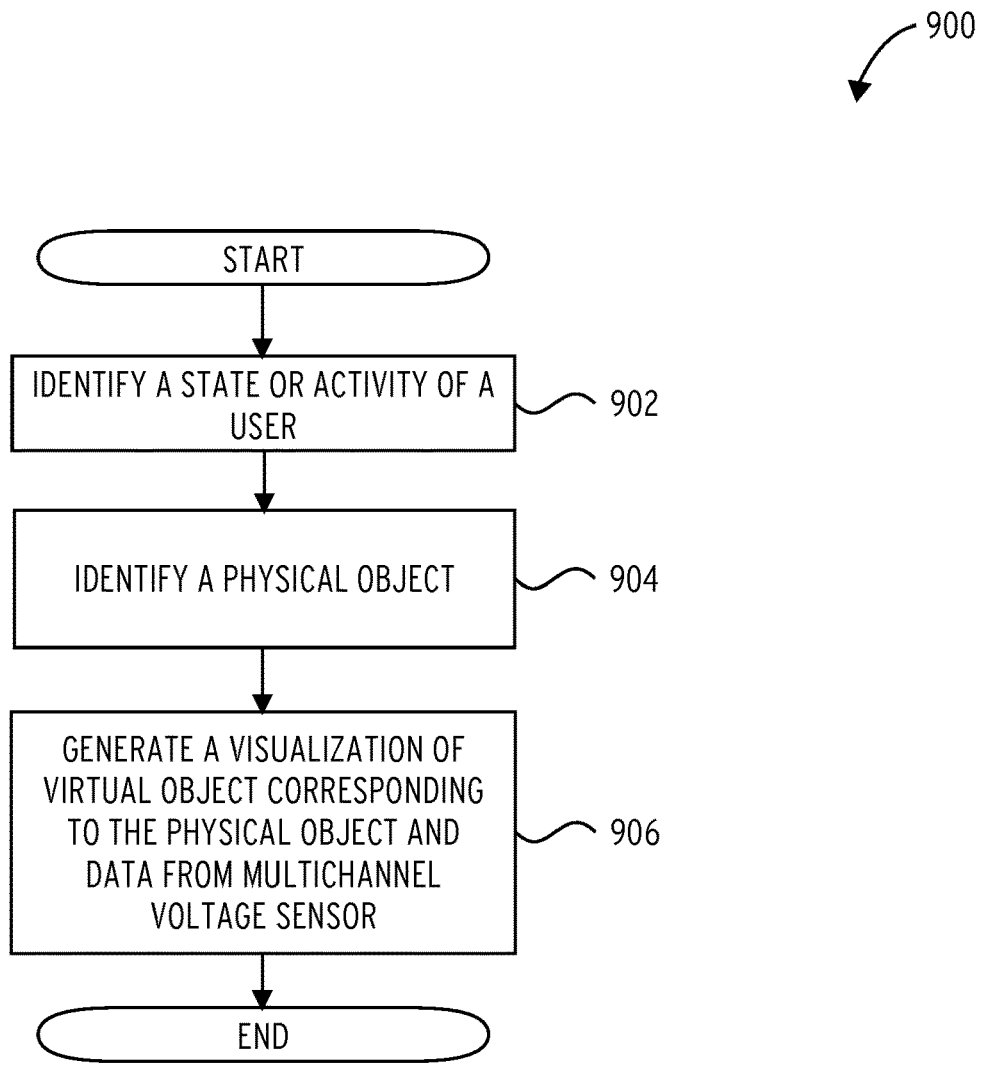
FIG. 9 is a flow diagram of a method for generating augmented reality content based on an analysis of biometric data from a multichannel voltage recording device, according to some example embodiments.

FIG. 9 is a flow diagram of a method 900 for generating augmented reality content based on an analysis of biometric data from a multichannel voltage recording device, according to some example embodiments.

In block 902, the display device 102 identifies a state (or a change of state) or activity (e.g., mental state or mental activity) of the user based on the voltage outputs of multichannel voltage recording device 114 connected to the forehead of the user 110. The output may include, for example, electric brain waves. In one example embodiment, block 902 may be performed using the multichannel voltage recording application 310 of the display device 102 of FIG. 1.

In block 904, the display device 102 identifies the physical object 112 based on an image of the physical object 112 captured with the sensors 302 of the display device 102. In one example embodiment, block 904 may be performed by the reference identifier module 404 that identifies a visual reference on the physical object 112.

In block 906, the augmented reality application 312 generates and displays a virtual object engaged (e.g., overlaid on top of) with an image of the physical object 112. The virtual object corresponds to the visual reference and the state or activity of the user as determined in block 902. In one example embodiment, the virtual object generation module 406 renders the virtual object based a position of the display device 102 relative to the physical object 112.

Figure 10:
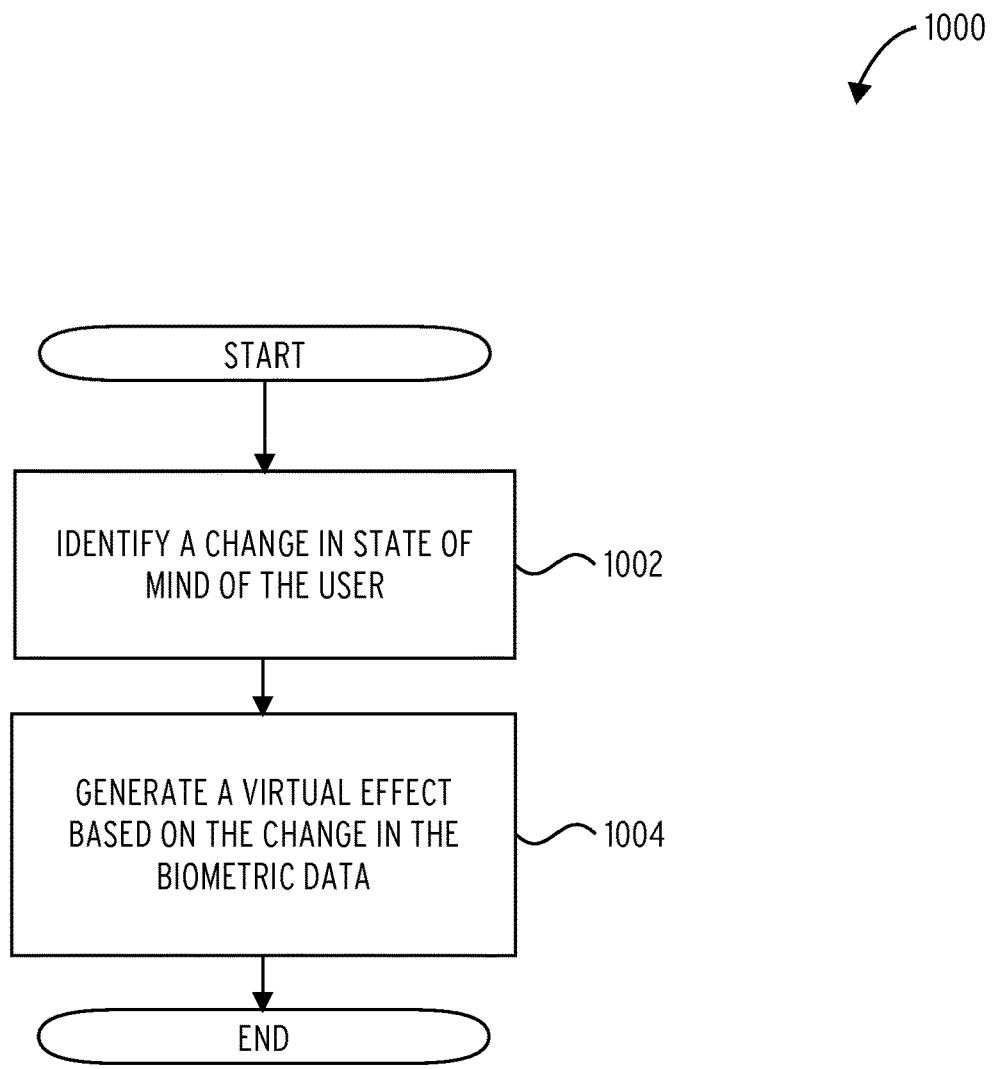
FIG. 10 is a flow diagram of a method for generating augmented reality content based changes of biometric data from a multichannel voltage recording device, according to some example embodiments.

FIG. 10 is a flow diagram of a method 1000 for generating augmented reality content based changes of biometric data from a multichannel voltage recording device, according to some example embodiments.

At block 1002, the display device 102 identifies a change in the level of state of mind of the user 110 based on a change in the intensity of outputs of sensors 302 coupled to the user 110. In one example embodiment, block 1002 may be performed using the multichannel voltage recording application 310 of the display device 102 of FIG. 1.

At block 1004, the display device 102 displays a different virtual object or a virtual effect in the display based on the change in the state or activity of the user 110 (e.g., change in power spectral density of the output of the sensors). In other words, an action may be performed on the virtual object in the display based on the change in the state or activity of the user 110. The virtual object may be manipulated based on the change in outputs of the multichannel voltage recording device 114. For example, the color of the virtual object may change from red to blue as the user becomes more relaxed. The virtual object may spin faster as the user becomes more stressed. The door of a virtual car may open as the user becomes more visually focused on the location of the door on the display. In one example embodiment, block 1004 may be implemented with the virtual object generation module 406.

Figure 11:
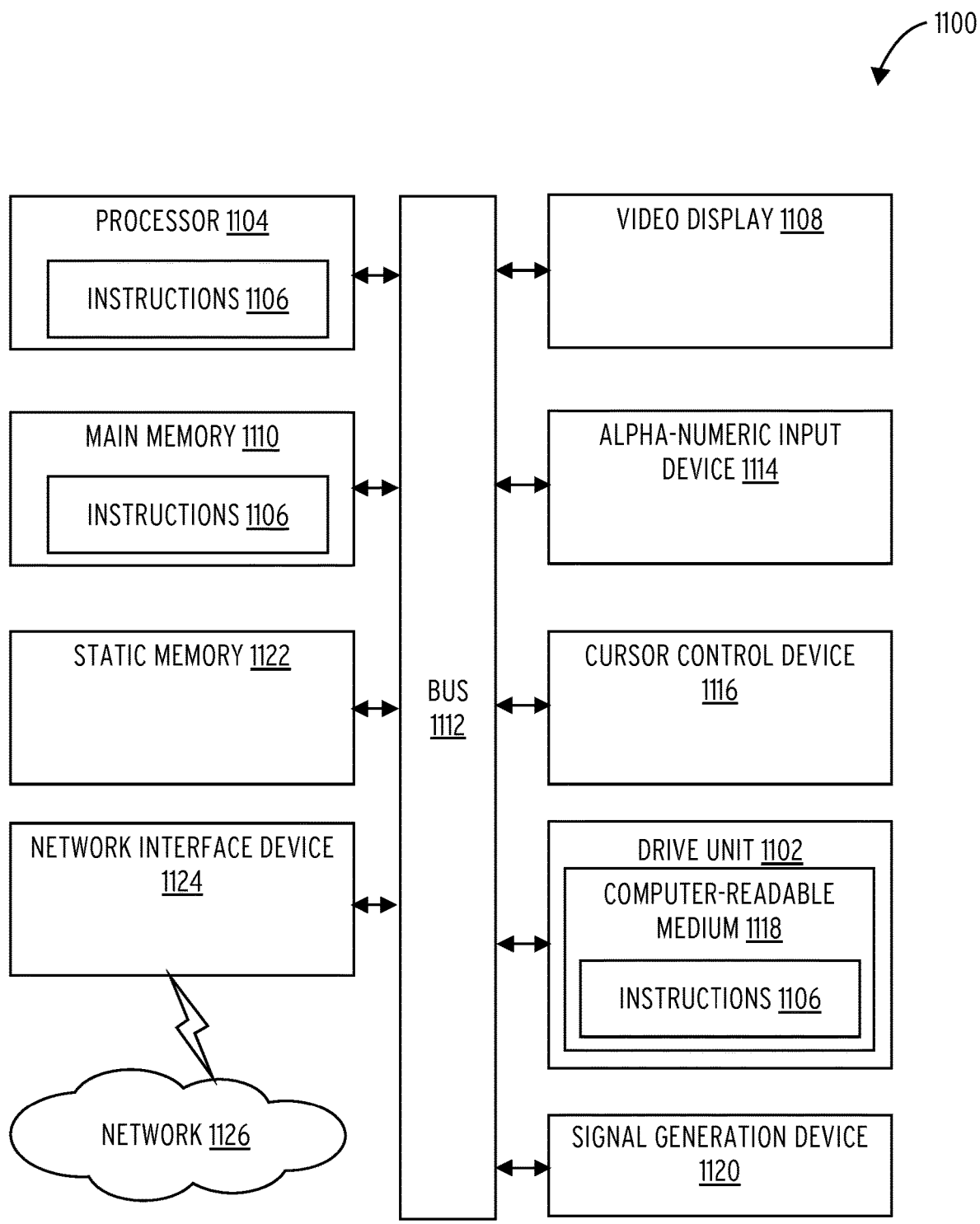
FIG. 11 a block diagram illustrating components of a machine, according to some example embodiments, able to read instructions from a machine-readable medium and perform any one or more of the methodologies discussed herein.

FIG. 11 is a block diagram illustrating components of a machine 1100, according to some example embodiments, able to read instructions 1106 from a computer-readable medium 1118 (e.g., a non-transitory machine-readable medium, a machine-readable storage medium, a computer-readable storage medium, or any suitable combination thereof) and perform any one or more of the methodologies discussed herein, in whole or in part. Specifically, the machine 1100 in the example form of a computer system (e.g., a computer) within which the instructions 1106 (e.g., software, a program, an application, an applet, an app, or other executable code) for causing the machine 1100 to perform any one or more of the methodologies discussed herein may be executed, in whole or in part.

In alternative embodiments, the machine 1100 operates as a standalone device or may be communicatively coupled (e.g., networked) to other machines. In a networked deployment, the machine 1100 may operate in the capacity of a server machine or a client machine in a server-client network environment, or as a peer machine in a distributed (e.g., peer-to-peer) network environment. The machine 1100 may be a server computer, a client computer, a personal computer (PC), a tablet computer, a laptop computer, a netbook, a cellular telephone, a smartphone, a set-top box (STB), a personal digital assistant (PDA), a web appliance, a network router, a network switch, a network bridge, or any machine capable of executing the instructions 1106, sequentially or otherwise, that specify actions to be taken by that machine. Further, while only a single machine is illustrated, the term "machine" shall also be taken to include any collection of machines that individually or jointly execute the instructions 1106 to perform all or part of any one or more of the methodologies discussed herein.

The machine 1100 includes a processor 1104 (e.g., a central processing unit (CPU), a graphics processing unit (GPU), a digital signal processor (DSP), an application specific integrated circuit (ASIC), a radio-frequency integrated circuit (RFIC), or any suitable combination thereof), a main memory 1110, and a static memory 1122, which are configured to communicate with each other via a bus 1112. The processor 1104 contains solid-state digital microcircuits (e.g., electronic, optical, or both) that are configurable, temporarily or permanently, by some or all of the instructions 1106 such that the processor 1104 is configurable to perform any one or more of the methodologies described herein, in whole or in part. For example, a set of one or more microcircuits of the processor 1104 may be configurable to execute one or more modules (e.g., software modules) described herein. In some example embodiments, the processor 1104 is a multicore CPU (e.g., a dual-core CPU, a quad-core CPU, or a 128-core CPU) within which each of multiple cores behaves as a separate processor that is able to perform any one or more of the methodologies discussed herein, in whole or in part. Although the beneficial effects described herein may be provided by the machine 1100 with at least the processor 1104, these same beneficial effects may be provided by a different kind of machine that contains no processors (e.g., a purely mechanical system, a purely hydraulic system, or a hybrid mechanical-hydraulic system), if such a processor-less machine is configured to perform one or more of the methodologies described herein.

The machine 1100 may further include a video display 1108 (e.g., a plasma display panel (PDP), a light emitting diode (LED) display, a liquid crystal display (LCD), a projector, a cathode ray tube (CRT), or any other display capable of displaying graphics or video). The machine 1100 may also include an alpha-numeric input device 1114 (e.g., a keyboard or keypad), a cursor control device 1116 (e.g., a mouse, a touchpad, a trackball, a joystick, a motion sensor, an eye tracking device, or other pointing instrument), a drive unit 1102, a signal generation device 1120 (e.g., a sound card, an amplifier, a speaker, a headphone jack, or any suitable combination thereof), and a network interface device 1124.

The drive unit 1102 (e.g., a data storage device) includes the computer-readable medium 1118 (e.g., a tangible and non-transitory machine-readable storage medium) on which are stored the instructions 1106 embodying any one or more of the methodologies or functions described herein. The instructions 1106 may also reside, completely or at least partially, within the main memory 1110, within the processor 1104 (e.g., within the processor's cache memory), or both, before or during execution thereof by the machine 1100. Accordingly, the main memory 1110 and the processor 1104 may be considered machine-readable media (e.g., tangible and non-transitory machine-readable media). The instructions 1106 may be transmitted or received over a network 1126 via the network interface device 1124. For example, the network interface device 1124 may communicate the instructions 1106 using any one or more transfer protocols (e.g., hypertext transfer protocol (HTTP)).

In some example embodiments, the machine 1100 may be a portable computing device (e.g., a smart phone, tablet computer, or a wearable device), and have one or more additional input components (e.g., sensors or gauges). Examples of such input components include an image input component (e.g., one or more cameras), an audio input component (e.g., one or more microphones), a direction input component (e.g., a compass), a location input component (e.g., a global positioning system (GPS) receiver), an orientation component (e.g., a gyroscope), a motion detection component (e.g., one or more accelerometers), an altitude detection component (e.g., an altimeter), a biometric input component (e.g., a heartrate detector or a blood pressure detector), and a gas detection component (e.g., a gas sensor). Input data gathered by any one or more of these input components may be accessible and available for use by any of the modules described herein.

As used herein, the term "memory" refers to a machine-readable medium able to store data temporarily or permanently and may be taken to include, but not be limited to, random-access memory (RAM), read-only memory (ROM), buffer memory, flash memory, and cache memory. While the computer-readable medium 1118 is shown in an example embodiment to be a single medium, the term "machine-readable medium" should be taken to include a single medium or multiple media (e.g., a centralized or distributed database, or associated caches and servers) able to store instructions. The term "machine-readable medium" shall also be taken to include any medium, or combination of multiple media, that is capable of storing the instructions 1106 for execution by the machine 1100, such that the instructions 1106, when executed by one or more processors of the machine 1100 (e.g., processor 1104), cause the machine 1100 to perform any one or more of the methodologies described herein, in whole or in part. Accordingly, a "machine-readable medium" refers to a single storage apparatus or device, as well as cloud-based storage systems or storage networks that include multiple storage apparatus or devices. The term "machine-readable medium" shall accordingly be taken to include, but not be limited to, one or more tangible and non-transitory data repositories (e.g., data volumes) in the example form of a solid-state memory chip, an optical disc, a magnetic disc, or any suitable combination thereof. A "non-transitory" machine-readable medium, as used herein, specifically does not include propagating signals per se. In some example embodiments, the instructions 1106 for execution by the machine 1100 may be communicated by a carrier medium. Examples of such a carrier medium include a storage medium (e.g., a non-transitory machine-readable storage medium, such as a solid-state memory, being physically moved from one place to another place) and a transient medium (e.g., a propagating signal that communicates the instructions 1106).

The following enumerated embodiments describe various example embodiments of methods, machine-readable media, and systems (e.g., machines, devices, or other apparatus) discussed herein.

A first embodiment provides a device (e.g., a multichannel voltage recording device) comprising:
at least three electrodes disposed across a conductive material, the at least three electrodes configured to be coupled to a skin of a user of the multichannel voltage recording device and configured to form at least two recording channels; and
a frame configured to support equal distribution of the conductive material around each electrode that is configured to receive a driven right leg (DRL) signal based on the voltage signals from the at least three electrodes and the at least two recording channels.

A second embodiment provides a device according to the first embodiment, further comprising:
a driven right leg (DRL) circuit coupled to the conductive material.

A third embodiment provides a device according to the second embodiment, wherein the driven right leg (DRL) circuit is configured to receive the voltage signals from the at least three electrodes and generate the DRL signal to the conductive material.

A fourth embodiment provides a device according to the third embodiment, wherein the conductive material includes at least one of a continuous sheet in which the at least three electrodes are placed and electrically-connected discrete units that surround each electrode.

A fifth embodiment provides a device according to the first embodiment, wherein the conductive material comprises at least one of a conductive silicon rubber and a biocompatible, conductive sheet material.

A sixth embodiment provides a device according to the first embodiment, further comprising an electrode insulator disposed around each electrode, the electrode insulator forming an insulating clearance between each electrode and the conductive material.

A seventh embodiment provides a device according to the first embodiment, wherein the at least three electrodes are evenly spaced in the frame.

An eighth embodiment provides a device according to the first embodiment, wherein the at least three electrodes comprise:
a first electrode corresponding to a first voltage channel positive input;
a second electrode corresponding to a second voltage channel positive input; and
a third electrode corresponding to a central voltage reference channel and a negative input for other channels,
wherein the DRL circuit receives the voltage signals corresponding to the first and second voltage channels, and generates the DRL signal based on the first, second, central voltage channels.

A ninth embodiment provides a device according to the first embodiment, further comprising:
a processor comprising a multichannel voltage recording application and a display application, the multichannel voltage recording application configured to determine a state of the user based on the DRL signal and the voltage signals from the at least three electrodes,
the display application configured to display a virtual object based on the state of the user.

A tenth embodiment provides a device according to the ninth embodiment, wherein the display application is configured to:
capture a reference identifier from a physical object with a camera;
identify a virtual object associated with the reference identifier;
display the virtual object in a display of the device; and
modify the virtual object based on the change in the state of the user.

What is claimed is:
1. A multichannel voltage recording device comprising:
at least three electrodes, wherein each of the at least three electrodes is surrounded by respective insulative material, comprising:

a first electrode of the at least three electrodes surrounded by first insulative material of the respective insulative material, a second electrode of the at least three electrodes surrounded by second insulative material of the respective insulative material, and a third electrode of the at least three electrodes surrounded by third insulative material of the respective insulative material, and wherein the at least three electrodes are disposed within a conductive material such that the respective insulative material of each of the at least three electrodes is surrounded by the conductive material, the at least three electrodes configured to be coupled to a skin of a user of the multichannel voltage recording device and capture voltage recordings from the user, and wherein at least two of the at least three electrodes provide a voltage signal including captured voltage recordings to an input portion of a driven right leg (DRL) circuit, and wherein the DRL circuit generates a DRL signal based on the voltage signal received from the at least two of the at least three electrodes; and a frame upon which the conductive material is affixed, the frame configured to support equal distribution of the conductive material around each electrode such that the respective insulative material of each electrode is surrounded equally by the conductive material, wherein the conductive material is configured to receive the DRL signal from an output portion of the DRL circuit and evenly distribute the DRL signal to each electrode via that conductive material to enable balanced and simultaneous noise compensation for each electrode.

2. The multichannel voltage recording device of claim 1, further comprising:

the output portion of the DRL circuit coupled to the conductive material.

3. The multichannel voltage recording device of claim 1, wherein the DRL circuit is configured to receive the voltage signals from the at least three electrodes and generate the DRL signal to be evenly distributed across the at least three electrodes via the conductive material.

4. The multichannel voltage recording device of claim 1, wherein the conductive material is a continuous sheet in which the at least three electrodes are placed.

5. The multichannel voltage recording device of claim 1, wherein the conductive material is comprised of one of a conductive silicon rubber or a biocompatible conductive sheet material.

6. The multichannel voltage recording device of claim 1, wherein the respective insulative material forms an insulating clearance between each electrode and the conductive material.

7. The multichannel voltage recording device of claim 1, wherein the at least three electrodes are evenly spaced in the frame.

8. The multichannel voltage recording device of claim 1, wherein:

the first electrode corresponds to a first voltage channel positive input;

the second electrode corresponds to a second voltage channel positive input; and the third electrode corresponds to a central voltage reference channel and a negative input for other channels, wherein the DRL circuit receives voltage signals corresponding to the first voltage channel positive input and the second voltage channel positive input, and generates the DRL signal based on the voltage signals.

9. The multichannel voltage recording device of claim 1, further comprising:

a processor comprising a multichannel voltage recording application and a display application, wherein the multichannel voltage recording application is configured to determine a state of the user based on the DRL signal and the voltage signals from the at least three electrodes, and the display application is configured to display a virtual object based on the state of the user.

10. The multichannel voltage recording device of claim 9, wherein the display application is configured to:

capture a reference identifier from a physical object with a camera;

identify a virtual object associated with the reference identifier;

display the virtual object in a display of a display device; and modify the virtual object based on a detected change to the state of the user.

* * * * *

UNITED STATES PATENT AND TRADEMARK OFFICE
CERTIFICATE OF CORRECTION

| | | |
|---|---|---|
| PATENT NO. | : 11,622,708 B2 | Page 1 of 1 |
| APPLICATION NO. | : 15/059129 | |
| DATED | : April 11, 2023 | |
| INVENTOR(S) | : Teresa Ann Nick et al. | |

It is certified that error appears in the above-identified patent and that said Letters Patent is hereby corrected as shown below:

In the Claims

In Column 21, Claim 1, Line 32, delete "via that" and insert -- via the --, therefor.

Signed and Sealed this
Twenty-eighth Day of January, 2025

Coke Morgan Stewart
*Acting Director of the United States Patent and Trademark Office*